(12) United States Patent
Kiritake (10) Patent No.: US 8,337,599 B2
(45) Date of Patent: Dec. 25, 2012

(54) OXYGEN CONCENTRATOR

(75) Inventor: Hisashi Kiritake, Yamaguchi (JP)

(73) Assignee: Teijin Pharma Limited, Tokyo (JP)

( * ) Notice: Subject to any disclaimer, the term of this patent is extended or adjusted under 35 U.S.C. 154(b) by 454 days.

(21) Appl. No.: 12/451,206

(22) PCT Filed: May 2, 2008

(86) PCT No.: PCT/JP2008/058688
§ 371 (c)(1),
(2), (4) Date: Oct. 30, 2009

(87) PCT Pub. No.: WO2008/136540
PCT Pub. Date: Nov. 13, 2008

(65) Prior Publication Data
US 2010/0071698 A1    Mar. 25, 2010

(30) Foreign Application Priority Data

May 7, 2007    (JP) .................. 2007-122329

(51) Int. Cl.
*B01D 53/047* (2006.01)
*A61M 16/10* (2006.01)

(52) U.S. Cl. ............... 96/22; 95/23; 95/130; 96/110; 96/114; 128/204.21

(58) Field of Classification Search ............. 96/110, 96/113, 114, 121; 95/1, 19, 22, 23, 130; 128/204.21, 204.26, 205.12, 204.22
See application file for complete search history.

(56) References Cited

U.S. PATENT DOCUMENTS 5,746,806 A * 5/1998 Aylsworth et al. .......... 95/8
(Continued)

FOREIGN PATENT DOCUMENTS

JP    02-157011 A    6/1990
(Continued)

OTHER PUBLICATIONS

Machine generated English translation of JP 2003-119004 A, published Apr. 2003.*

(Continued)

*Primary Examiner* — Frank Lawrence, Jr.
(74) *Attorney, Agent, or Firm* — Rader, Fishman & Grauer PLLC (57) ABSTRACT

The present invention relates to an oxygen concentrator in which a pulsation detection device for detecting pulsation of oxygen supplied and a control device for controlling an amount of air supplied from a compressor based on the detection results in a pressure swing adsorption-type oxygen concentrator, which is equipped with an adsorption bed filled with an adsorbent capable of selectively adsorbing nitrogen relative to oxygen, the compressor for supplying air to the adsorption bed, a channel switching valve to repeat in a constant timing an adsorption step, in which air is supplied from the compressor to the adsorption bed to isolate concentrated oxygen and a desorption step, in which the adsorption bed is evacuated to regenerate the adsorbent and a flow rate measuring device for determining a supply flow rate of concentrated oxygen produced and an amount of oxygen produced is controlled by a feedback with a flow rate sensor by itself after paying attention to variation of a product flow rate caused by suppressing an amount of oxygen produced, thereby realizing an apparatus to satisfy secondary performance such as miniaturization, low power consumption and silencing.

7 Claims, 2 Drawing Sheets

U.S. PATENT DOCUMENTS

| | | | |
|---|---|---|---|
| 5,871,564 A | 2/1999 | McCombs | |
| 6,629,525 B2 * | 10/2003 | Hill et al. | 128/202.26 |
| 7,455,717 B2 * | 11/2008 | Sprinkle | 95/22 |
| 7,585,351 B2 * | 9/2009 | Deane et al. | 95/19 |
| 7,682,428 B2 * | 3/2010 | Nawata et al. | 96/113 |
| 2002/0096174 A1 | 7/2002 | Hill et al. | |
| 2006/0174880 A1 | 8/2006 | Jagger et al. | |
| 2006/0230931 A1 | 10/2006 | Bliss et al. | |

FOREIGN PATENT DOCUMENTS

| | | | |
|---|---|---|---|
| JP | 06-031129 A | | 2/1994 |
| JP | 06-185468 A | | 7/1994 |
| JP | 11-207128 A | | 8/1999 |
| JP | 11-207128 A | * | 8/1999 |
| JP | 2000-060973 A | * | 2/2000 |
| JP | 2000-354630 A | | 12/2000 |
| JP | 2001-259341 A | | 9/2001 |
| JP | 2001-259342 A | | 9/2001 |
| JP | 2002-504022 A | | 2/2002 |
| JP | 2002-204918 A | | 7/2002 |
| JP | 2002-253676 A | | 9/2002 |
| JP | 2003-117330 A | | 4/2003 |
| JP | 2003-119004 A | * | 4/2003 |
| JP | 2004-209467 A | | 7/2004 |
| JP | 2005-312766 A | | 11/2005 |
| JP | 2005-324044 A | | 11/2005 |
| JP | 2006-329026 A | | 12/2006 |
| JP | 2007-44115 A | | 2/2007 |
| WO | WO-98/57728 A1 | | 12/1998 |

OTHER PUBLICATIONS

Machine generated English translation of JP 2000-060973 A, published Feb. 2000.*
Machine generated English translation of JP 2001-259341, published Sep. 2001.*
International Search Report mailed on Jun. 17, 2008.
European Search Report for Patent Application No. 08752571 dated Sep. 21, 2011 (EPO).
Office Action for Japanese Patent Application No. 2007-055929 mailed Sep. 20, 2011 (Japan).
Office Action issued in Japanese Patent Application No. 2007-055930, dated Dec. 13, 2011.
Office Action in Japanese Patent Application No. 2007-072466, dated Feb. 7, 2012.
Office Action in Japanese Patent Application No. 2009-513036, issued on Dec. 20, 2011.
Office Action issued in corresponding Japanese Application No. 2007-055929, mailed Jul. 10, 2012.

* cited by examiner

OXYGEN CONCENTRATOR

TECHNICAL FIELD

The present invention relates to a pressure swing adsorption-type oxygen concentrator using an adsorbent, which preferentially adsorbs nitrogen relative to oxygen and in particular a medical oxygen concentrator used in an oxygen inhalation method for patients with chronic respiratory diseases and the like.

BACKGROUND ART

In recent years, the number of patients suffering from diseases of respiratory organs such as asthma, pulmonary emphysema, chronic bronchitis and the like has tended to increase and oxygen inhalation therapy has been available as one of most effective therapies for them. Such oxygen inhalation therapy is a treatment method for patients to inhale oxygen-enriched air. As the supply source of the oxygen and the air, an oxygen concentrator, a liquefied oxygen cylinder, an oxygen gas cylinder and the like are known but an oxygen concentrator has become dominant for home oxygen therapy because of convenience and easiness in maintenance and control.

An oxygen concentrator is an apparatus in which about 21% oxygen present in air is concentrated in a high concentration to supply to a user. Such apparatuses include a membrane type oxygen concentrator using a polymer membrane, which selectively permeates oxygen, a pressure swing adsorption-type oxygen concentrator using an adsorbent, which selectively adsorbs nitrogen relative to oxygen, an apparatus electrochemically separating oxygen contained in air to supply and the like. The pressure swing adsorption-type oxygen concentrator is mainly used in a market because oxygen concentrated to 90% or more can be obtained in good yield.

The pressure swing adsorption-type oxygen concentrator is an apparatus using an adsorption bed filled with molecular sieve zeolites such as 5A type zeolite, 13X type zeolite, Li-X type zeolite, MD-X type zeolite and the like as the adsorbent, which can selectively adsorb nitrogen relative to oxygen, supplying compressed air from a compressor to the adsorption bed to adsorb nitrogen under a pressurized condition and isolating unadsorbed oxygen as a concentrated-oxygen gas. Such an apparatus is generally equipped with two or more adsorption beds and can continuously produce oxygen by switching between the absorption step in which nitrogen is adsorbed by the adsorbent in the adsorption beds to produce unadsorbed oxygen and the desorption step in which nitrogen is regenerated by evacuating absorbed nitrogen by decompressing the other absorption beds.

The pressure swing adsorption method includes a PSA method, in which the pressure of the desorption step is reduced to an atmospheric pressure and a VPSA (vacuum pressure swing adsorption) method, in which an inner pressure of an adsorption cylinder is reduced to a vacuum level using a compressor in order to increase the regeneration rate of the adsorbent and both methods are used as an oxygen concentration method in a medical oxygen concentrator.

Such an oxygen concentrator is often used not only at hospital, but also at home as oxygen inhalation therapy for patients with chronic respiratory diseases. Accordingly, not only stable and consistent supply of a predetermined concentration of an oxygen-concentrated gas at a constant feed rate is required for the oxygen concentrator as main performance, but also requirement for the secondary performance such as low power consumption, quietness, miniaturization and the like are increasing taking into consideration the convenience of a user to the apparatus.

Among constitutional parts of the oxygen concentrator, a compressor consumes most of electric power used in the whole apparatus and at the same time, occupies a certain space within the enclosure as well as generates a major source of noise. A compressor used has to be miniaturized in order to realize such secondary performance of the apparatus. However, miniaturization of the compressor is accompanied by the reduction of a flow rate and compression performance in the compressor, resulting in disadvantage with reduced allowance to maintain adsorption-desorption performance of the oxygen concentrator.

As a means to achieve lowering power consumption of an oxygen concentrator and realize a high yield of oxygen, Japanese Patent Application Laid-Open No. H11-207128 describes an apparatus, in which the number of rotation of a compressor is controlled in response to a predetermined flow rate of oxygen to control a supply flow rate of raw material air and a switching timing between an adsorption step and a desorption step is determined by controlling opening and closing of a switching valve to supply air in an optimum pressurized time.

Japanese Patent Application Laid-Open No. 2001-259341 also describes an apparatus provided with a function, in which the number of rotation of a compressor is controlled by use of an inverter based on an oxygen concentration of an oxygen-concentrated gas produced and a predetermined flow rate of oxygen, and the power consumption is suppressed at a low flow rate.

As an apparatus to shorten a pressure rising time of an adsorption cylinder in the adsorption step and to improve the adsorption efficiency in an early stage, Japanese Patent Application Laid-Open No. H6-31129 discloses a gas separation apparatus, in which the number of rotation of the motor driving the compressor is increased for a predetermined period at the adsorption step, while otherwise the number of rotation is controlled in a normal value.

DISCLOSURE OF INVENTION

An oxygen concentrator is equipped with a product tank to temporarily store concentrated oxygen produced in a downstream of an adsorption bed in order to respond to variation of a supply flow rate at the time of switching to a predetermined flow rate of oxygen. This provides a buffering function responding to a change of a supply flow rate and performs feedback control of increasing the number of rotation of the compressor to increase an amount of oxygen produced when the pressure becomes lower than a predetermined pressure by detecting pressure variation within the product tank with a pressure sensor.

Suppressing an amount of oxygen produced to a requisite minimum enables to reduce a flow rate required to a compressor and to install a smaller compressor with low power consumption on an oxygen concentrator. A product tank itself can be accordingly miniaturized. On the other hand, allowance of maintaining the primary function of the apparatus for a change of setting of the flow rate of oxygen supplied and a change of use environment with the apparatus such as a temperature, a pressure and the like. When various detection device such as an oxygen concentration sensor, a flow rate sensor, a pressure sensor and the like are installed to respond to variations regarding to such problems, installation of a new detection device and a control mechanism may lead to increased size and cost.

The present invention is to solve above problems and to realize an apparatus to satisfy secondary performance such as miniaturization, low power consumption and quietness by performing feedback control of the amount produced with a flow rate sensor alone, focusing on variation of a product flow rate caused by suppressing the amount of oxygen produced.

The present invention provides an oxygen concentrator in which a pulsation detection device for detecting pulsation of oxygen supplied and a control device to control an amount of air supplied from a compressor based on the detection results in a pressure swing adsorption oxygen type concentrator, which is equipped with an adsorption bed filled with an adsorbent capable of selectively adsorbing nitrogen relative to oxygen, a compressor for supplying air to the adsorption bed, a channel switching valve to repeat in a constant timing an adsorption step, in which air is supplied from the compressor to the adsorption bed to isolate concentrated oxygen and a desorption step, in which the adsorption bed is evacuated to regenerate the adsorbent, and a flow rate measuring device for determining a supply flow rate of concentrated oxygen produced.

The present invention also provides the oxygen concentrator in which the pulsation detection device is the flow rate measuring device with a function of determining a peak flow rate and/or bottom flow rate of concentrated oxygen supplied and the control device of an increase or decrease of an amount of air supplied from the compressor when the peak flow rate or the bottom flow rate per predetermined time exceeds a predetermined range of a threshold value.

The present invention also provides the oxygen concentration method in which the method is provided with step 1 of controlling an amount of the pressurized air supplied based on a predetermined value of a supply flow rate of an oxygen-concentrated gas produced, step 2 of detecting pulsation of the oxygen-concentrated gas and step 3 of controlling the amount of the pressurized air based on detection results of the pulsation in the pressure swing adsorption type oxygen concentration method, in which the adsorption step of supplying the pressurized air to an adsorption bed filled with an adsorbent capable of selectively adsorbing nitrogen relative oxygen to isolate an oxygen-concentrated gas and the desorption step of evacuating the adsorption bed to regenerate the adsorbent are repeated in a constant timing, producing an oxygen-concentrated gas.

The present invention also provides the oxygen concentration method in which step 2 of detecting such pulsation of an oxygen-concentrated gas is a step of determining a peak flow rate and/or bottom flow rate of an oxygen-concentrated gas supplied and detecting whether or not the peak flow rate value or the bottom flow rate value per predetermined time is within a predetermined range of a threshold value and then controls an increase or decrease of an amount of the pressurized air when exceeding the range of threshold values, and the step judges as pulsation being occurred when the peak flow rate value or the bottom flow rate value exceeds a range of ±5% relative to the predetermined flow rate value and compares the detection result in a peak flow rate value (Lp) and a bottom flow rate value (Lb) in a single sequence of adsorption-desorption in the pressure swing adsorption method with the predetermined threshold value, in particular, with the predetermined threshold value based on a rate of flow rate variation represented by the equation of (peak flow rate value (Lp)−bottom flow rate value (Lb))/predetermined flow rate value to control an increase or decrease of an amount of the pressurized air supplied when exceeding the range of the threshold value. Pulsation of the oxygen-concentrated gas can be measured by not only the flow rate value of the oxygen-concentrated gas supplied, but also a value of pressure thereof.

BEST MODE FOR CARRYING OUT THE PRESENT INVENTION

Figure 1:
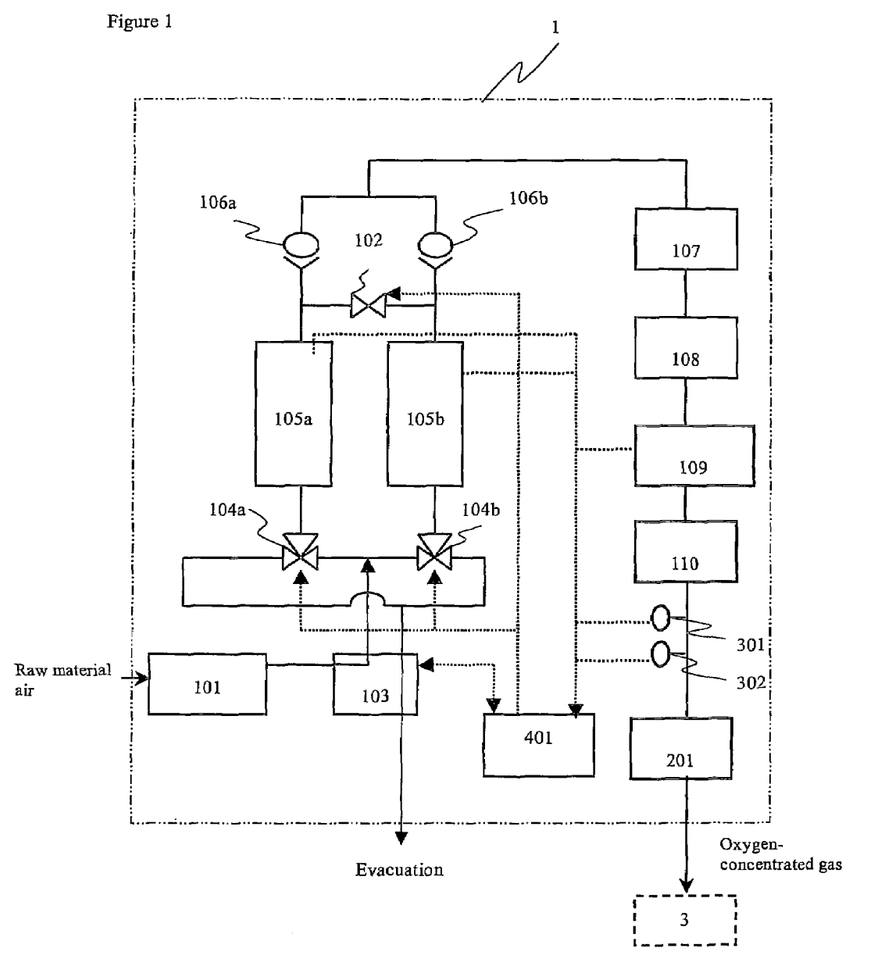
FIG. 1 shows a schematic diagram of a vacuum pressure swing adsorption (VPSA) type oxygen concentrator in an example of illustrative embodiment of an oxygen concentrator of the present invention.

An example of illustrative embodiment of the oxygen concentrator of the present invention is described using the drawings below. FIG. 1 is a schematic diagram of an apparatus constitution illustrating a two-column vacuum pressure swing adsorption (VPSA) type oxygen concentrator as an embodiment of the present invention.

In FIG. 1, 1 represents an oxygen concentrator and 3 indicates an oxygen concentrator and a user (patient) inhaling a humidified oxygen-concentrated gas. The pressure swing adsorption-type oxygen concentrator 1 is equipped with an external air intake filter 101, compressor 103 with a function of compression and evacuation, three-way electromagnetic valves 104a and 104b as a channel switching valve, adsorption cylinders 105a and 105b, check valves 106a and 106b, a product tank 107, a pressure regulating valve 108, a flow rate setting device 109 and a filter 110. This allows to separate oxygen from raw material air brought in from outside to concentrate and produce an oxygen-concentrated gas.

Raw material air brought in from outside is first flown from an air inlet equipped with an external air intake filter 101 to eliminate foreign particles such as dust and the like into inside of the enclosure of the apparatus. At this time, ordinary air contains about 21% oxygen, about 77% nitrogen, 0.8% argon and 1.2% gases such as steam and other gases. Such apparatus is an apparatus for concentrating oxygen gas from air required as a breathing gas to isolate.

For isolating such oxygen-concentrated gas, an adsorbent capable of selectively adsorbing nitrogen molecules relative to oxygen molecules is used as an adsorption bed. Specifically, molecular sieve zeolites such as 5A type zeolite, 13X-type zeolite, Li-X type zeolite, MD-X type zeolite and the like can be used as the nitrogen adsorbent. Raw material air is pressurized by the compressor 103 to supply to the adsorption cylinders 105a or 105b filled with the zeolite type adsorbent, while sequentially switching between the targeted adsorption cylinders 105a and 105b with the switching valves 104a and 104b, in which about 77% nitrogen gas contained in raw material air is selectively adsorbed and removed under a pressurized condition in the adsorption cylinder.

The above adsorption cylinders 105a and 105b are formed by a cylindrical vessel filled with the above adsorbent and, though a single column type, two-column type or multi-column type oxygen concentrator using three or more adsorption cylinders are generally available depending on the number of the adsorption cylinder used, a two-column type adsorption system described in FIG. 1 or multi-column adsorption system is preferably used in order to continuously and effectively produce an oxygen-concentrated gas from raw material air.

A rotating-type air compressor such as screw-type, rotary-type, scroll-type air compressors and the like may be used in some cases as compressor 103 described above in addition to a two-headed reciprocating-type air compressor as a compressor with both compression and evacuation functions. The power source of a motor to drive the compressor 103 may be alternate current or direct current.

An oxygen-concentrated gas containing as a main component the oxygen gas, which was not adsorbed on a zeolite adsorbent in the above adsorption cylinder 105 is flown into the product tank 107 through the check valves 106*a* and 106*b* installed to prevent backflow to the adsorption cylinder 105.

From the zeolite adsorbent filled in the adsorption cylinder, it has to desorb and remove nitrogen molecules once adsorbed from the adsorbent in order to adsorb the nitrogen gas again from freshly introduced raw material air. For this purpose, it is connected by the three-way electromagnetic valves (switch valves) 104*a* and 104*b* with a vacuum line of the compressor 103 to switch from a pressurized condition achieved by the compressor 103 to an evacuated and depressurized condition to desorb the nitrogen gas adsorbed to regenerate the adsorbent. In this desorption step, part of the oxygen-concentrated gas may be further flown back as a purge gas through a pressure equalizing valve 102 from the product outlet side of the adsorption cylinder in the adsorption step to the adsorption cylinder in the desorption step in order to increase desorption efficiency.

An oxygen-concentrated gas is thus produced from raw material air and stored in the product tank 107. The oxygen-concentrated gas stored in the product tank 107 contains, for example, a concentrated oxygen gas highly concentrated to a level of 95%, and the pressure and supply flow rate thereof are controlled by a pressure regulating valve 108, the flow rate setting device 109 and the like to supply to a humidifier 201, from which a humidified oxygen-concentrated gas is supplied to the patient.

A no-water supply type hollow fiber humidifier, in which a moisture permeation membrane module with a moisture permeation membrane intakes moisture from external air to supply to an oxygen-concentrated gas in dry condition, a bubble-type humidifier using water, or a surface evaporation type humidifier can be used as such a humidifier 201.

In the VPSA type oxygen concentrator, when one adsorption cylinder 105*a* is under the pressurized adsorption step, the other adsorption cylinder 105*b* is under the evacuation-desorption step, thus sequentially switching between the adsorption step and the desorption step in a form of an antiphase, respectively, to continuously produce oxygen.

A flow rate setting device 109 allows to supply oxygen at a stable flow rate, provided that an amount of oxygen produced from the adsorption cylinder can be maintained such that a pressure of the product tank 107 is sufficiently higher than a pressure required to maintain the pressure constant at an outlet of the pressure regulating valve 108.

Secondary performance of the apparatus taking into consideration convenience of a user with the apparatus such as reduction of power consumption, quietness and miniaturization of the oxygen concentrator is determined by a type of compressor used and operation control method.

One of such methods is a method of controlling a flow rate of a compressor such that an amount of oxygen produced in the adsorption bed is kept at minimum requisite, thereby enabling to suppress power consumption. This also simultaneously leads to quietness of the apparatus and miniaturization of the compressor used. It further becomes more effective, when the amount of oxygen produced is controlled by a control device 401 based on a setting flow rate of the oxygen-concentrated gas determined by the flow rate setting device 109.

In order to realize this, when an amount of oxygen produced is controlled such that an inner pressure of the product tank is slightly higher than the pressure required to maintain the pressure constant at the outlet of the pressure regulating valve controlling an amount of oxygen produced in every flow rate value, feedback control of the amount of oxygen produced cannot be followed and the pressure in the product tank is lowered temporarily to cause a pulsating flow of oxygen gas supplied when a change with a setting value of a flow rate temporarily causes increasing an amount of oxygen withdrawn. In order to prevent this situation, a method of constantly monitoring the pressure in the product tank 107 may be considered for controlling the amount of oxygen produced, but this requires new installation of a pressure sensor to measure a pressure in the product tank.

The oxygen concentrator of the present invention comprises the features with a pulsation detection device for detecting pulsation of oxygen supplied and a control device for controlling an amount of air supplied from a compressor depending on the presence or absence of pulsation. The pulsation detection device is a flow rate sensor 302 provided with a function to measure a peak flow rate and a bottom flow rate of concentrated oxygen supplied, and the control device 401 is used to control an increase or decrease of the amount of air supplied from the compressor 103 when the peak flow rate value or bottom flow rate value per a predetermined time exceeds a predetermined range of a threshold value. For example, it is judged as pulsation being occurred when the peak flow rate value or the bottom flow rate value exceeds a range of ±5% relative to a predetermined value of the flow rate value, followed by controlling to increase the number of rotation with an electric motor in order to increase the amount of air supplied from the compressor.

The flow rate sensor 302 include various flow rate sensors such as an electromagnetic type, mechanical type, ultrasonic type or thermal type sensor and the like. The ultrasonic type flow rate sensor can simultaneously measure an oxygen concentration. A pulsating flow is detected by detecting and calculating a peak flow rate value (Lp) and a bottom flow rate value (Lb) in a single sequence of adsorption-desorption in the pressure swing adsorption method, since a pressure of oxygen produced is varied with every sequence of adsorption-desorption. Comparison with the predetermined threshold value can be managed by a rate of a flow rate variation ((Lp−Lb)/predetermined value of flow rate) in addition to comparison with the absolute value.

Pulsation can be detected, in addition to the flow rate sensor 302, by detecting pressure variation when the pressure sensor 301 is provided in the downstream of a pressure regulating valve.

An existing sensor is thus used to detect pulsation of oxygen gas supplied and control the amount of oxygen produced based on the detection results, thereby minimizing a flow rate supplied by a compressor required for production of oxygen and realizing various secondary effects to satisfy compliance of a patient for requesting an oxygen concentrator with miniaturization of a compressor, reduction of power consumption with an apparatus, silencing and the like.

Miniaturization of a compressor reduces a mechanical remaining power of the compressor with compression performance and vacuum performance, resulting in being susceptible to a use temperature of environment. At the start-up of an oxygen concentrator, load to a driving motor of the compressor is increased by applying pressure load, friction resistance and the like to a compression part of the compressor as compared with the steady operation. The magnitude of static resistive load widely varies with a use environment of the oxygen concentrator and the compressor might not start up in particular under a low temperature environment in winter. Its cause can be attributed to an increase of a torque required for the start-up and an increase of a starting current for the driving motor, yielding a condition of torque shortage and occasionally no start-up of the apparatus.

A method to suppress such a compressor load at the start-up of an oxygen concentrator can be realized by the oxygen concentrator in which a pressure equalizing channel with a pressure equalizing valve to equalize a pressure between adsorption cylinders in the downstream of the adsorbent cylinder and the start-up control device to start up the compressor in a state where the pressure equalizing valve is open in a pressure swing adsorption-type oxygen concentrator, which is provided with plural adsorption cylinders filled with an adsorbent capable of selectively adsorbing nitrogen relative to oxygen, a compressor for supplying pressurized air to the adsorption cylinder and a channel switching device for sequentially switching a channel between the compressor and each adsorption cylinder and further repeating in a predetermined timing the adsorption step, in which pressurized air is supplied to each adsorption cylinder to isolate concentrated oxygen and the desorption step, in which each adsorption cylinder is evacuated to regenerate the adsorbent.

In further more detail, it is realized by an oxygen concentrator comprising the features, in which such an adsorption cylinder is two adsorption cylinders, the channel switching device is an electromagnetic valve to switch among each adsorption cylinder, compressor and exhaust pipe, the start-up control device is a device to control opening and closing of the pressure equalizing valve and the electromagnetic valve such that the compressor is communicated through the electromagnetic valve with the adsorption cylinder at the adsorption step side for a predetermined time at the start-up of the compressor as well as the pressure equalizing valve is opened to communicate the adsorption cylinder at the desorption step side through the electromagnetic valve with the exhaust pipe, and in particular, the channel switching device is a three-way electromagnetic valve, and an oxygen concentrator comprising the features, in which such a start-up control device is a control device to the start up the compressor at the number of rotation in the start-up lower than the number of rotation in a stationary state.

Figure 2:
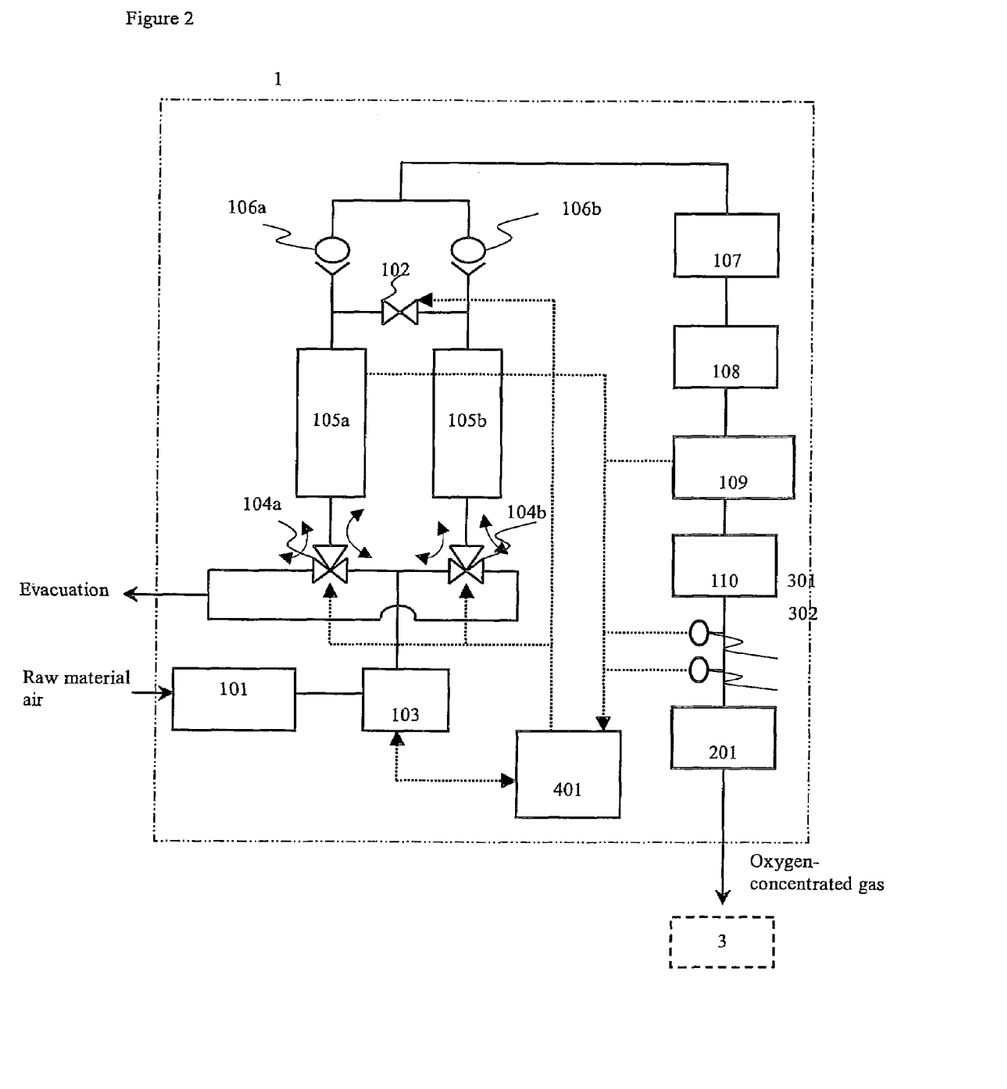
FIG. 2 also shows a schematic diagram of a pressure swing adsorption (PSA) type oxygen concentrator in another example of illustrative embodiment of an oxygen concentrator of the present invention.

FIG. 2 is a schematic diagram of apparatus constitution illustrating a two-column pressure swing adsorption (PSA) type oxygen concentrator. The apparatus has the same constitution except an evacuation channel in the desorption step is connected with a channel open to atmosphere in the PSA type oxygen concentrator in FIG. 2, whereas it goes through a vacuum evacuation line of the compressor 103 in the VPSA type oxygen concentrator shown in FIG. 1. The adsorption cylinder 105 under pressurized condition is therefore evacuated by the three-way electromagnetic valves (switch valve) 104a and 104b to an atmospheric pressure condition to desorb nitrogen gas adsorbed to regenerate the adsorbent. In this desorption step, the oxygen-concentrated gas may be further flown back as a purge gas through the pressure equalizing valve 102 from the product end side of the adsorption cylinder in the adsorption step in order to increase its desorption efficiency.

Since the adsorbent used in the pressure swing adsorption method depends on the pressure and a gas is purified from the product end side of the adsorption cylinder in the beginning of starting the oxygen concentrator before the pressure in the adsorption cylinder is not sufficiently raised, the oxygen concentration of the gas produced in the beginning of the start-up becomes a lower value as compared with an oxygen-concentrated gas at high concentration of 90 to 95% in a stationary state and thereby requiring a longer time for the oxygen concentration to reach a stationary state after completing gas exchange in the product tank 107. At the start-up of the apparatus of the present invention, the control device 401 is used to control opening of the pressure equalizing valve 102 in the downstream of the adsorption cylinder 105 (product end side) together with the start-up of the compressor 103 and for example, pressurized air is fed to the adsorption cylinder 105a in the adsorption step to recover the gas produced in the beginning through the pressure equalizing valve 102 from the product end side of the adsorption cylinder 105b in the desorption step. Since the pressure in the adsorption cylinder 105a is generally raised in a few seconds, the pressure equalizing valve 102 is closed thereafter to start up the ordinary adsorption step storing concentrated oxygen of, for example, 90% through the check valve 106a in the product tank.

Higher load is applied at the start-up of the compressor as compared with a stationary operation condition. At the start-up under a low temperature condition in winter or the like in particular, a drive torque of the compressor is increased to generate occasionally a condition, in which the compressor cannot start up when the power is turned on. The torque required for the start-up of the compressor is generally high to increase a starting current of the driving motor.

Since the apparatus of the present invention starts up in such a condition as the adsorption cylinder 105a in the adsorption step is communicated through the pressure equalizing valve 102 with the adsorption cylinder 105b in the desorption step at the time of driving the compressor, little pressure load is applied to the compression part of the compressor, resulting in the start-up under the condition with substantially no pressure load, and enabling to start up without causing a raise of a rush current beyond necessity as above.

At the start-up of the apparatus, the control device 401 controlling the start-up can therefore start up the compressor at the number of rotation at the start-up lower than the number of rotation in a stationary state.

The control device 401 of the oxygen concentrator controls various operations in the stationary state. It detects a predetermined value of the flow rate setting device 109, a flow rate value of the product gas by the flow rate sensor 302 and the oxygen concentration of the produced oxygen-concentrated gas by the oxygen concentration sensor 301, and controls the number of revolution in an electric motor for compressor 103 by control device 401 to control a rate of airflow to be supplied to adsorption cylinder 195. When a predetermined flow rate is set at a low flow rate, lowering the number of revolution suppresses the amount of oxygen generated, leading to reduction of electric power consumption. Timings of switching the switch valves 104a and 104b and the pressure equalizing valve 102 are controlled to change the time in adsorption-desorption sequences, realizing to optimize the oxygen formation.

Miniaturization of the compressor is effective in reducing noise generated by an oxygen concentrator, on which it is installed. However, its effect is effective in a stationary operation, but large noise is generated when starting and stopping the apparatus. Various measures are taken in a medical oxygen concentrator for reduction of noise and prevention of vibration. For example, a change from a reciprocating compressor to a scroll-type compressor or helical-type compressor with low noise, a shielding method with use of a box and a duct, and a method of installing a resonance type or expansion type silencer on an intake pipe and an exhaust pipe, or gluing an acoustic material to an enclosure, are used. As described above, various methods from improving the compressor itself to modifying the enclosure and installing the silencer have been used as the measures to reduce noise in the stationary operation. However, any measures in the start-up and stoppage of the apparatus have not been taken at all. When starting the apparatus, a patient with respiratory disease as a user of the oxygen concentrator generally gets up, but when stopping the apparatus, the patient is in sleep and a care-giver possibly stops the operation so that noise or vibration in stoppage may possibly causes waking up the patient and people in sleep. There is therefore a need for a technology to prevent the pressure swing adsorption-type oxygen concentrator from generating noise and vibration in stopping the apparatus.

Such problems can be solved by the oxygen concentrator in which a stop-control device that controls switching of the channel switching device for adjusting an inner pressure of the adsorption cylinder to a normal pressure when stopping the apparatus and controls stopping of the driving of a compressor at the time when the inner pressure of the adsorption cylinder is equal to or lower than a predetermined pressure after receiving a command signal of stopping the apparatus in the pressure swing adsorption-type oxygen concentrator, which is provided with plural adsorption cylinders filled with an adsorbent capable of selectively adsorbing nitrogen relative to oxygen, a compressor for supplying pressurized air to the adsorption cylinder and a channel switching device to sequentially switch a channel between the compressor and each adsorption cylinder and repeat in a predetermined timing the adsorption step, in which pressurized air is supplied to each adsorption cylinder to isolate concentrated oxygen and the desorption step, in which each adsorption cylinder is evacuated to regenerate the adsorbent.

They may be solved by a device, in which a pressure equalizing channel equipped with a pressure equalizing valve to communicate the product end of the adsorption cylinder at the pressurized side with that of the adsorbent cylinder at the evacuation-desorption side is further provided and the stop control device is a device to open the pressure equalizing valve based on a command signal of stopping the apparatus and control stoppage of driving the compressor in the condition keeping which the equalizing valve is open or a device to control switching of the channel switching device such that the adsorption cylinder at the pressurized side and the adsorption cylinder at the evacuation-desorption side are communicated with the vacuum line of the compressor and the pressurized line of the compressor, respectively, to control stoppage of driving of the compressor at the same time or immediately after implementing the switching control.

Specifically the stop control device is a device that controls stoppage of driving of the compressor at the time when an inner pressure of the adsorption cylinder is equal to or less than 50% of the maximum pressure value thereof and in particular, is applied to an oxygen concentrator in which the adsorption cylinder is two adsorption cylinders, the compressor is a compressor equipped with the function to supply pressurized air to the adsorption cylinder as well as evacuate to vacuum and a channel switching device is provided in order to sequentially switch a channel between the compressor and each adsorption cylinder and repeat in a predetermined timing the adsorption step, in which pressurized air is supplied to each adsorption cylinder to isolate concentrated oxygen and the desorption step, in which each adsorption cylinder is evacuated to vacuum to regenerate the adsorbent.

Such an embodiment is described using the oxygen concentrator described in FIG. 1. In a VPSA type oxygen concentrator, when one adsorption cylinder 105a is under the pressurized adsorption step, the other adsorption cylinder 105b is under the evacuation-desorption step, thus sequentially switching between the adsorption step and the desorption step in a form of antiphase, respectively, to continuously produce oxygen.

When stopping the apparatus, the control device 401 that controls switching of the channel switching valves 104a and 104b controls stoppage of driving of the compressor 103 at the time when an inner pressure of the adsorption cylinder is equal to or lower than a predetermined pressure after receiving a command signal of stopping the apparatus in order to adjust the inner pressure of the adsorption cylinders 105a and 105b to a normal pressure. That is, the compressor is controlled to stop not at the time when a pressure difference is large immediately after completion of the adsorption-desorption step, but at the time when a pressure difference between adsorption cylinders is small after a predetermined time, thus realizing silencing and suppression of vibration when stopped.

Specifically, using a pressure equalizing channel equipped with the pressure equalizing valve 102 to communicate the product end of the adsorption cylinder 105a at the pressurized side with that of the adsorption cylinder 105b at the evacuation-desorption side, the stop control device 401 opens the pressure equalizing valve 102 based on the command signal of stopping the apparatus and stops driving of the compressor in the condition of the pressure equalizing purging step, in which part of the product gas is used to purge the adsorption cylinder 105b at the desorption side. Opening the pressure equalizing valve 102 lowers the pressure in the adsorption cylinder 105a at the pressurized side to 50% or less of the maximum pressure and the compressor can be stopped in this condition to automatically discharge a gas with a residual pressure, realizing to silently stop the apparatus.

The control device 401 controls switching of the channel switching valves 104a and 104b based on the command signal of stopping the apparatus such that the adsorption cylinder 105a at the pressurized side and the adsorption cylinder 105b at the evacuation-desorption side are communicated with the vacuum line of the compressor 103 and the pressurized line of the compressor, respectively and controls stoppage of driving of the compressor at the same time or immediately after controlling for switching between the adsorption step and the desorption step, thus enabling to stop the compressor around an atmospheric pressure and realize silencing and damping when stopping the apparatus.

Points to remember are further appended when stopping the oxygen concentrator. When stopping a VPSA type oxygen concentrator, there is generally a need to remember many points such as deterioration of the adsorbent during stoppage, stabilization of the operation at an early stage after restart and the like. Especially, considerations on discharging moisture in an adsorption bed, a compressor, a pipe and the like have not been taken in a conventional apparatus when stopping operation of the apparatus, causing problems such as deterioration of the adsorbent by moisture absorption due to moisture remained in the adsorption bed after stopping the operation, dew condensation, rusting in the compressor, a switching valve and the like. A method of discharging moisture during stoppage after completion of the evacuation step may be considered, but in this case, moisture in one column can be discharged, but moisture may be accumulated in other column. A check valve installed between the adsorption bed and the product tank cannot respond to purge the product gas from the product tank, generating a need to install a new electromagnetic valve. Accordingly, a technology to prevent moisture absorption and dew condensation in the adsorption bed and the switching valve after stopping the apparatus becomes important.

Such problems can be solved by an oxygen concentrator in which there is provided a stop-control device that controls switching of the channel switching device for adjusting an inner pressure of the adsorption cylinder to a normal pressure when stopping the apparatus that is a pressure swing adsorption-type oxygen concentrator, which is provided with plural adsorption cylinders filled with an adsorbent capable of selectively adsorbing nitrogen relative to oxygen, a compressor with a function to supply pressurized air to the adsorption cylinder as well as evacuate to vacuum, and a channel switching device for sequentially switching a channel between the compressor and each adsorption cylinder thereby repeating the adsorption step in a predetermined timing, in which pressurized air is supplied to each adsorption cylinder to isolate concentrated oxygen and the desorption step, in which each adsorption cylinder is evacuated to regenerate the adsorbent.

Further, an oxygen concentrator can be mentioned as an embodiment in which the stop control device is a device that controls switching of the channel switching device based on the stop signal of the compressor such that the adsorption cylinder at the pressurized side and the adsorption cylinder at the evacuation-desorption side are communicated with the vacuum line of the compressor and the pressurized line of the compressor, respectively, and in particular, the stop control device controls switching of the channel switching control device based on the stop signal of the compressor such that the adsorption cylinder at the pressurized side and the adsorption cylinder at the evacuation-desorption side are communicated with the vacuum line of the compressor and the pressurized line of the compressor, respectively, followed by controlling to switch the channel switching control device such that the adsorption cylinder at the pressurized side and the adsorption cylinder at the evacuation-desorption side are communicated with the pressurized line of the compressor and the vacuum line of the compressor, respectively.

Furthermore, as an example of a preferred embodiment is considered an oxygen concentrator in which a pressure equalizing channel equipped with a pressure equalizing valve to communicate the product end of the adsorption cylinder at the pressurized side with that of the adsorption cylinder at the evacuation-desorption side, in which the stop control device is a device that controls stopping of driving of the compressor in a condition where the pressure equalizing valve is open, the adsorption cylinder is two adsorption cylinders and the channel switching device is composed by a three-way valve that switches the adsorption cylinder with the pressurized line or vacuum line of the compressor and connect the adsorption cylinder with the vacuum line of the compressor when turning off the power source.

In such an oxygen concentrator, operation of both adsorption beds at the pressurized-adsorption step side and the evacuation-desorption step side in the VPSA type oxygen concentrator are stopped in the atmospheric pressure condition, enabling to prevent gas in the apparatus from migration when stopping the apparatus, in particular prevent highly humid external air from flowing into the adsorption bed at the evacuation side. Evacuation of pressurized air to atmospheric pressure can also prevent in advance the occurrence dew condensation of pressurized air associated with temperature decrease of the apparatus after stopping the apparatus.

When the three-way valve that switches between two column adsorption beds pressurization/evacuation of the compressor are adopted in a connecting system, in which both adsorption cylinders are communicated with the vacuum line of compressor when turning off the power source, a small amount of gas with residual pressure remained in the adsorption bed can be discharged through a plate valve at the vacuum line side of the compressor with a loose seal to maintain the inside of the apparatus at normal pressure.

Such an embodiment is described using the oxygen concentrator described in FIG. 1. In the VPSA type oxygen concentrator, when one adsorption cylinder 105a is under pressurized-adsorption step, other adsorption cylinder 105b is under evacuation-desorption step, thus the adsorption step and the desorption step are sequentially switched in a form of antiphase, respectively, to continuously produce oxygen. An inner pressure of the adsorption cylinder can be stopped at atmospheric pressure if the compressor 103 can be stopped at the time when the pressure of the adsorption beds 105a and 105b become zero (atmospheric pressure), respectively, but control of both columns for stopping at atmospheric condition is difficult since the compressor 103 is practically continued to drive for some time by inertia even after receiving a stop signal. The signal for stopping the apparatus itself is preferably controlled to stop the compressor not at the time when a pressure difference is high immediately after completion of the adsorption-desorption step, but at the time when the pressure difference between columns is small after a predetermined time from a viewpoint of the efficiency to return both columns to the atmospheric pressure. This is also preferred from a viewpoint of silencing and prevention of vibration when stopping the compressor.

There is a method to release a pressure of the adsorption bed to the atmosphere after stopping the apparatus, but in case of the VPSA apparatus, the evacuation line is connected with the vacuum line of the compressor 103 so that evacuation is stopped as stopping the compressor.

In the apparatus of the present invention, the channel switching valves 104a and 104b, in which the adsorption cylinder 105a at the pressurized side and the adsorption cylinder 105b at the evacuation-desorption side are connected with the pressurized line of the compressor and the vacuum line of the compressor, respectively, is controlled by switching the channel switching valves 105a and 105b, to communicate the adsorption cylinder at the pressurized side and the adsorption cylinder at the evacuation-desorption side with the vacuum line of the compressor and the pressurized line of the compressor, respectively, based on a stop signal of the compressor 103 in order to adjust the inner pressure of the columns to normal pressure when stopping the apparatus. This utilizes the compressor run by the inertia to evacuate the adsorption cylinder at the pressurized side and pressurize the adsorption cylinder at the evacuation side. Such operation accomplishes pressure equalization with a normal pressure of the adsorption cylinder, but a residual pressure might remain so that the channel switching valve is further switched again such that the adsorption cylinder at the pressurized side and the adsorption cylinder at the evacuation-desorption side are communicated with the pressurized line of the compressor and the vacuum line of the compressor, respectively, to evacuate gas with residual pressure.

The pressure equalizing valve 102 to communicate the product end of the adsorption cylinder at the pressurized side with that of the adsorption cylinder at the evacuation-desorption side is provided to generally perform the pressure equalization step and product purging step in the adsorption-desorption step. In the present invention, the stop-control device 401 simultaneously controls to stop the driving of the compressor in the condition where the pressure equalization valve is open and equalizes not only the pressure at raw material end, but also the pressure at both product ends of the adsorption cylinder.

As shown in FIG. 1, when two adsorption cylinders are used and a channel is composed by using the three-way valve that switches the adsorption cylinder with the pressure line or the vacuum line of the compressor as the channel switching device, the channel is preferably set such that the adsorption cylinder is connected with the vacuum line of the compressor when turning off the power source. The channel open to a normal pressure when turning off the power source is connected with the adsorption cylinder and the vacuum line of the compressor, thereby enabling to evacuate gas with residual pressure through a plate valve at the vacuum line side of the compressor with loose seal and maintain a normal pressure within the apparatus even if operation of the adsorption bed is stopped under pressurized condition.

Effect of the Invention

The oxygen concentrator of the present invention detects pulsation of oxygen gas supplied with an existing sensor to control an amount of oxygen produced based on detection results, thereby enabling to minimize a flow rate supplied by a compressor required for production of oxygen and realizing various secondary effects to satisfy compliance of a patient required for an oxygen concentrator such as miniaturization of a compressor, reduction of power consumption and silencing with the apparatus.

When load torque of the compressor is increased at the time of the start-up due to reduction of power consumption, the adsorption cylinder at the pressurized side is communicated with the adsorption cylinder at the desorption side through a pressure equalizing valve so that pressurized air is not used for pressurizing an inner pressure of the adsorption cylinder, but is controlled to flow as is in the evacuation side, thus enabling to the start-up the compressor in the condition substantially free from a pressure load. Increase of the starting current therefore does not occur at the time of the start-up, thereby contributing to reduction of the rush current at the time of the start-up. Further, a gas with low oxygen concentration containing impurities produced in a product end of the adsorption cylinder at the pressurized side in an early stage of the start-up can be recovered through the pressure equalizing valve to the adsorption cylinder at the desorption step side, allowing to prevent the gas with low oxygen concentration from flowing to the product tank side and to supply a gas with high oxygen concentration of 90% to a user in an early stage.

Furthermore, by controlling stoppage of driving of the compressor at the time when the inner pressure of the adsorption cylinder is at a predetermined pressure, in particular at 50% or less of the maximum pressure of the adsorption cylinder, the noise and vibration of the compressor can be prevented. For this purpose, driving of the compressor can be stopped by opening the pressure equalizing valve based on a command signal of stopping the apparatus in the condition of the pressurized purge step where the pressure equalizing valve is open or stopped at the same time or immediately after controlling of switching the channel switching device such that the adsorption cylinder at the pressurized side and the adsorption cylinder at the evacuation-desorption side are communicated with the vacuum line of the compressor and the pressurized line of the compressor, respectively.

The invention claimed is:

1. A pressure swing adsorption-type oxygen concentrator comprising an adsorption bed filled with an adsorbent capable of selectively adsorbing nitrogen relative to oxygen, a compressor for supplying air to the adsorption bed, a channel switching valve to repeat in a constant timing an adsorption step, in which air is supplied from the compressor to the adsorption bed to isolate concentrated oxygen and a desorption step, in which the adsorption bed is evacuated to regenerate the adsorbent, a flow rate setting device for setting a supply flow rate of the concentrated oxygen produced, and a flow rate measuring device for determining a supply flow rate of concentrated oxygen produced, wherein a pulsation detection device for detecting pulsation of oxygen supplied, detecting a variation of a flow rate measured by the flow rate measuring device to a flow rate provided by the flow rate setting device, and a control device of an amount of air supplied from the compressor based on the pulsation detection results are provided, wherein the pulsation detection device is the flow rate measuring device with a function of determining a peak flow rate and/or bottom flow rate of the concentrated oxygen supplied and the control device is a device to control an increase or decrease of an amount of air supplied from the compressor, when the peak flow rate value or the bottom flow rate value per predetermined time exceeds a predetermined range of a threshold value, and wherein the pulsation detection device is a device to detect and calculate the peak flow rate value (Lp) and the bottom flow rate value (Lb) in a single sequence of adsorption-desorption in the pressure swing adsorption method to make comparison with a predetermined threshold value.

2. A pressure swing adsorption-type oxygen concentrator comprising an adsorption bed filled with an adsorbent capable of selectively adsorbing nitrogen relative to oxygen, a compressor for supplying air to the adsorption bed, a channel switching valve to repeat in a constant timing an adsorption step, in which air is supplied from the compressor to the adsorption bed to isolate concentrated oxygen and a desorption step, in which the adsorption bed is evacuated to regenerate the adsorbent, a flow rate setting device for setting a supply flow rate of the concentrated oxygen produced, and a flow rate measuring device for determining a supply flow rate of concentrated oxygen produced, wherein a pulsation detection device for detecting pulsation of oxygen supplied, detecting a variation of a flow rate measured by the flow rate measuring device to a flow rate provided by the flow rate setting device, and a control device of an amount of air supplied from the compressor based on the pulsation detection results are provided, wherein the pulsation detection device is the flow rate measuring device with a function of determining a peak flow rate and/or bottom flow rate of the concentrated oxygen supplied and the control device is a device to control an increase or decrease of an amount of air supplied from the compressor, when the peak flow rate value or the bottom flow rate value per predetermined time exceeds a predetermined range of a threshold value and wherein the pulsation detection device is a device to make comparison with the predetermined threshold value based on a rate of a flow rate variation represented by the equation of (peak flow rate value (Lp)−bottom flow rate value (Lb))/predetermined flow rate value.

3. A pressure swing adsorption type oxygen concentration method for producing an oxygen-concentrated gas by repeating in a constant timing an adsorption step to supply pressurized air to an adsorption bed filled with an adsorbent capable of selectively adsorbing nitrogen relative to oxygen to isolate an oxygen-concentrated gas and a desorption step to evacuate the adsorption bed to regenerate the adsorbent, comprising, step 1 of controlling an amount of the pressurized air supplied based on a predetermined value of a supply flow rate of an oxygen-concentrated gas produced, step 2 of detecting pulsation of the oxygen-concentrated gas, detected a variation of a flow rate measured by a flow rate measuring device to a flow rate provided by a flow rate setting device, and step 3 of controlling the amount of the pressurized air based on detection results of the pulsation, wherein step 2 of detecting pulsation of the oxygen-concentrated gas is a step to determine the peak flow rate and/or bottom flow rate of the oxygen-concentrated gas supplied and detect whether or not the peak flow rate value or the bottom flow rate value is within a predetermined range of a threshold value, and to control an increase or decrease of an amount of the pressurized air supplied when the rate exceeds the threshold value and wherein step 2 of detecting pulsation of the oxygen-concentrated gas detects and calculates the peak flow rate value (Lp) and the bottom flow rate value (Lb) in a single sequence of the adsorption-desorption in the pressure swing adsorption method to make comparison with a predetermined threshold value.

4. A pressure swing adsorption type oxygen concentration method for producing an oxygen-concentrated gas by repeating in a constant timing an adsorption step to supply pressurized air to an adsorption bed filled with an adsorbent capable of selectively adsorbing nitrogen relative to oxygen to isolate an oxygen-concentrated gas and a desorption step to evacuate the adsorHption bed to regenerate the adsorbent, comprising, step 1 of controlling an amount of the pressurized air supplied based on a predetermined value of a supply flow rate of an oxygen-concentrated gas produced, step 2 of detecting pulsation of the oxygen-concentrated gas, detected a variation of a flow rate measured by a flow rate measuring device to a flow rate provided by a flow rate setting device, and step 3 of controlling the amount of the pressurized air based on detection results of the pulsation, wherein step 2 of detecting pulsation of the oxygen-concentrated gas is a step to determine the peak flow rate and/or bottom flow rate of the oxygen-concentrated gas supplied and detect whether or not the peak flow rate value or the bottom flow rate value is within a predetermined range of a threshold value, and to control an increase or decrease of an amount of the pressurized air supplied when the rate exceeds the threshold value and wherein step 2 of detecting pulsation of the oxygen-concentrated gas makes comparison with the predetermined threshold value based on a rate of flow rate variation represented by the equation of (peak flow rate value (Lp)−bottom flow rate value (Lb))/predetermined flow rate value.

5. A pressure swing adsorption type oxygen concentration method for producing an oxygen-concentrated gas by repeating in a constant timing, an adsorption step to supply pressurized air to an adsorption bed filled with an adsorbent capable of selectively adsorbing nitrogen relative to oxygen to isolate an oxygen-concentrated gas and a desorption step to evacuate the adsorption bed to regenerate the adsorbent, wherein step 1 of controlling an amount of the pressurized air supplied based on a predetermined value of a supply flow rate of an oxygen-concentrated gas produced, step 2 of detecting pulsation of the oxygen-concentrated gas is a step to determine the peak pressure and/or bottom pressure of the oxygen-concentrated gas supplied and detect whether or not the peak pressure value or the bottom pressure value per a predetermined time is within a predetermined range of a threshold value, and step 3 of controlling the amount of the pressurized air based on detection results of the pulsation, wherein step 2 of detecting pulsation of the oxygen-concentrated gas detects and calculates the peak flow rate value (Lp) and the bottom flow rate value (Lb) in a single sequence of the adsorption-desorption in the pressure swing adsorption method to make comparison with a predetermined threshold value.

6. A pressure swing adsorption type oxygen concentration method for producing an oxygen-concentrated gas by repeating in a constant timing an adsorption step to supply pressurized air to an adsorption bed filled with an adsorbent capable of selectively adsorbing nitrogen relative to oxygen to isolate an oxygen-concentrated gas and a desorption step to evacuate the adsorption bed to regenerate the adsorbent, comprising, step 1 of controlling an amount of the pressurized air supplied based on a predetermined value of a supply flow rate of an oxygen-concentrated gas produced, step 2 of detecting pulsation of the oxygen-concentrated gas, detected a variation of a flow rate measured by a flow rate measuring device to a flow rate provided by a flow rate setting device, and step 3 of controlling the amount of the pressurized air based on detection results of the pulsation, wherein step 2 of detecting pulsation of the oxygen-concentrated gas is a step to determine the peak flow rate and/or bottom flow rate of the oxygen-concentrated gas supplied and detect whether or not the peak flow rate value or the bottom flow rate value is within a predetermined range of a threshold value, and to control an increase or decrease of an amount of the pressurized air supplied when the rate exceeds the threshold value wherein the pulsation detection device judges as pulsation being occurred when the peak flow rate value or the bottom flow rate value exceeds a range of ±5% relative to a predetermined value of the flow rate value and controls to increase an amount of the pressurized air supplied and wherein step 2 of detecting pulsation of the oxygen-concentrated gas detects and calculates the peak flow rate value (Lp) and the bottom flow rate value (Lb) in a single sequence of the adsorption-desorption in the pressure swing adsorption method to make comparison with a predetermined threshold value.

7. A pressure swing adsorption type oxygen concentration method for producing an oxygen-concentrated gas by repeating in a constant timing an adsorption step to supply pressurized air to an adsorption bed filled with an adsorbent capable of selectively adsorbing nitrogen relative to oxygen to isolate an oxygen-concentrated gas and a desorption step to evacuate the adsorption bed to regenerate the adsorbent, comprising, step 1 of controlling an amount of the pressurized air supplied based on a predetermined value of a supply flow rate of an oxygen-concentrated gas produced, step 2 of detecting pulsation of the oxygen-concentrated gas, detected a variation of a flow rate measured by a flow rate measuring device to a flow rate provided by a flow rate setting device, and step 3 of controlling the amount of the pressurized air based on detection results of the pulsation, wherein step 2 of detecting pulsation of the oxygen-concentrated gas is a step to determine the peak flow rate and/or bottom flow rate of the oxygen-concentrated gas supplied and detect whether or not the peak flow rate value or the bottom flow rate value is within a predetermined range of a threshold value, and to control an increase or decrease of an amount of the pressurized air supplied when the rate exceeds the threshold value,
wherein the pulsation detection device judges as pulsation being occurred when the peak flow rate value or the bottom flow rate value exceeds a range of ±5% relative to a predetermined value of the flow rate value and controls to increase an amount of the pressurized air supplied and wherein step 2 of detecting pulsation of the oxygen-concentrated gas makes comparison with the predetermined threshold value based on a rate of flow rate variation represented by the equation of (peak flow rate value (Lp)−bottom flow rate value (Lb))/predetermined flow rate value.

* * * * *